United States Patent
Fan et al.

(10) Patent No.: US 8,802,607 B2
(45) Date of Patent: Aug. 12, 2014

(54) LIQUID CLEANING COMPOSITIONS CONTAINING LONG-CHAIN FATTY ALCOHOLS

(75) Inventors: Aixing Fan, Bridgewater, NJ (US); Jeffrey Mastrull, Middlesex, NJ (US); Edward Simpson, Sayreville, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/992,747

(22) PCT Filed: Dec. 9, 2010

(86) PCT No.: PCT/US2010/059676
§ 371 (c)(1),
(2), (4) Date: Jun. 9, 2013

(87) PCT Pub. No.: WO2012/078159
PCT Pub. Date: Jun. 14, 2012

(65) Prior Publication Data
US 2013/0261037 A1    Oct. 3, 2013

(51) Int. Cl.
*C11D 1/29* (2006.01)
*C11D 1/90* (2006.01)
*C11D 3/22* (2006.01)
*A61K 8/34* (2006.01)
*A61K 8/40* (2006.01)
*A61K 8/46* (2006.01)
*A61K 8/73* (2006.01)

(52) U.S. Cl.
USPC ........... 510/155; 510/123; 510/125; 510/126; 510/127; 510/151; 510/153; 510/159; 510/426; 510/433; 510/437; 510/474; 510/490; 510/492; 510/499; 510/535; 424/70.13; 424/70.19; 424/70.24

(58) Field of Classification Search
USPC ......... 510/123, 125, 126, 127, 151, 153, 155, 510/159, 426, 433, 437, 474, 490, 492, 499, 510/535; 424/70.13, 70.19, 70.24
See application file for complete search history.

(56) References Cited

U.S. PATENT DOCUMENTS

| 3,929,678 | A | 12/1975 | Laughlin et al. |
| 4,209,449 | A | 6/1980 | Mayhew et al. |
| 5,104,643 | A | 4/1992 | Grollier et al. |
| 5,132,037 | A | 7/1992 | Greene et al. |

(Continued)

FOREIGN PATENT DOCUMENTS

| DE | 19814608 | 9/1999 |
| EP | 0355368 | 2/1994 |

(Continued)

OTHER PUBLICATIONS

Cognis Corporation, "Luscious Whipped Facial Cleansing Cream," retrieved from internet Oct. 13, 2010.

(Continued)

*Primary Examiner* — Brian P Mruk
(74) *Attorney, Agent, or Firm* — Michael F. Morgan

(57) ABSTRACT

A composition comprising a) a surfactant comprising an anionic surfactant; b) at least 8 weight % of the composition of a C12-18 fatty alcohol, and c) water. A cleansing method includes applying the composition to skin or hair and washing, and optionally rinsing with water.

14 Claims, 1 Drawing Sheet

(56) References Cited

U.S. PATENT DOCUMENTS

| | | |
|---|---|---|
| 5,147,574 A | 9/1992 | MacGilp et al. |
| 5,607,678 A | 3/1997 | Moore et al. |
| 5,632,978 A | 5/1997 | Moore et al. |
| 5,670,471 A | 9/1997 | Amalric et al. |
| 5,683,972 A | 11/1997 | Zocchi |
| 5,908,617 A | 6/1999 | Moore et al. |
| 5,929,024 A | 7/1999 | Stringer et al. |
| 5,994,280 A | 11/1999 | Giret et al. |
| 6,077,816 A | 6/2000 | Puvvada et al. |
| 6,087,320 A | 7/2000 | Urfer et al. |
| 6,906,016 B1 | 6/2005 | Tsaur |
| 6,977,082 B2 | 12/2005 | Seitz, Jr. et al. |
| 7,704,932 B2 | 4/2010 | Evans et al. |
| 2003/0083210 A1 | 5/2003 | Goldberg et al. |
| 2005/0136026 A1 | 6/2005 | Qiu et al. |
| 2006/0141014 A1* | 6/2006 | Eknoian et al. ............... 424/443 |
| 2007/0032393 A1 | 2/2007 | Patel et al. |
| 2008/0153727 A1 | 6/2008 | Tsaur et al. |
| 2008/0153729 A1 | 6/2008 | Tsaur et al. |
| 2008/0153730 A1 | 6/2008 | Tsaur et al. |
| 2009/0156450 A1 | 6/2009 | Tsaur |
| 2010/0062961 A1 | 3/2010 | Post et al. |
| 2010/0075881 A1 | 3/2010 | Tsaur |

FOREIGN PATENT DOCUMENTS

| | | |
|---|---|---|
| EP | 1718268 | 1/2008 |
| EP | 1994922 | 11/2008 |
| WO | WO 93/025650 | 12/1993 |
| WO | WO 94/017166 | 8/1994 |
| WO | WO 97/05857 | 2/1997 |
| WO | WO 2009/030594 | 3/2009 |
| WO | WO 2009/100262 | 8/2009 |
| WO | WO 2009/100276 | 8/2009 |
| WO | WO 2010/025898 | 3/2010 |

OTHER PUBLICATIONS

Cognis Corporation, "PLANTAREN® 2000 N UP" Product Data Sheet retrieved from internet 2013.

Colgate-Palmolive Co., MSDS for "Softsoap Body Wash, Pure Cashmere", http://householdproducts.nlm.nih.gov/cgi-bin/household/brands?tbl=brands&id=3008073 (MSDS Date: Jan. 2, 2008).

International Search Report and Written Opinion in International Application No. PCT/US10/059676, mailed Oct. 27, 2011.

International Search Report and Written Opinion in International Application No. PCT/US10/059683, mailed Oct. 27, 2011.

Proctor & Gamble Co., MSDS for "Olay Moisturizing Body Wash-Old Product", http://householdproducts.nlm.nih.gov/cgi-bin/household/brands?tbl=brands&id=16003086 (MSDS Date Apr. 4, 2000).

Thareja et al., 2011, "Development of an in situ rheological method to characterize fatty acid crystallization in complex fluids," Colloids & Surfaces A: Physiochemistry 388:12-20.

Unilever, MSDS for "Dove Sensitive Skin Moisturizing Body Wash, New", http://householdproducts.nlm.nih.gov/cgi-bin/household/brands?tbl=brands&id=12002018 (MSDS Date Oct. 21, 1997).

Unilever, MSDS for "Dove Ultra Moisturizing Body Wash", http://householdproducts.nlm.nih.gov/cgi-bin/household/brands?tbl=brands&id=12002005 (MSDS Date Aug. 2, 1995).

Unilever, 2010, "Whipped Souffle Blackberry Cream Body Wash." Mintel GNPD Accession No. 1328265.

Written Opinion in International Application No. PCT/US10/059676, mailed Nov. 20, 2012.

Written Opinion in International Application No. PCT/US10/059683, mailed Nov. 20, 2012.

* cited by examiner

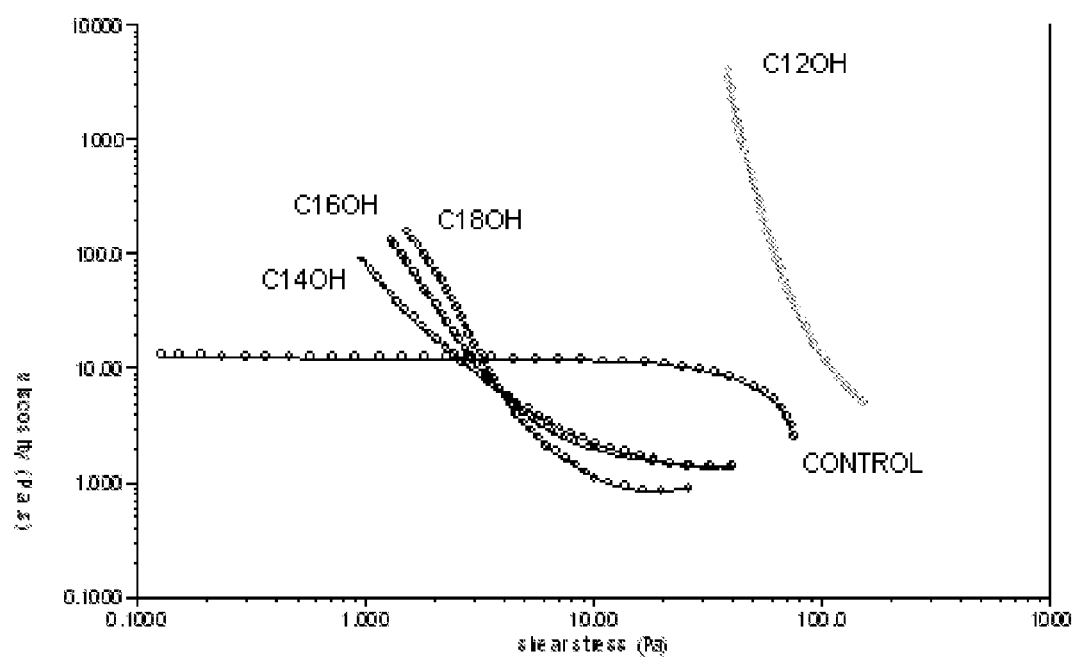

LIQUID CLEANING COMPOSITIONS CONTAINING LONG-CHAIN FATTY ALCOHOLS

BACKGROUND

Shower gels, body washes, cleansing lotions, liquid soaps, and the like (hereinafter collectively referred to as "liquid cleaning compositions" be they liquids, gels, lotions or foams) have grown increasingly popular in recent times. Such compositions typically comprise a mixture of surfactants as skin cleaning agents. The performance of these compositions can be modified by modifying the interaction of the surfactants in the mixed surfactant system.

It is known to use salts to modify the packing of surfactants to achieve higher viscosity. See, e.g., Lin et al., "Spherical-To-Wormlike Micelle Transition In CTAB Solutions", J. Phys. Chem., 1994, 98, 5984-5993 and Yang, "Viscoelastic wormlike micelles and their applications", Current Opinion in Colloid & Interface Science 7 (2002) 276-281. With the addition of increasing concentrations of salt, the viscosity typically increases, reaches a maximum, and suddenly decreases. This observation is related to the formation of dense wormlike micelles (tighter packing which results in high viscosities) and then branched wormlike micelles (which causes the viscosity to drop).

However, high levels of salt cause the cleaning product to be stringy, and adversely affect the foam properties of the product.

It is therefore desired to increase the viscosity of liquid cleaning compositions and to create different compositional forms.

SUMMARY

An aqueous composition comprising: a) surfactants comprising a salt of a $C_{10-16}$ alcohol ethoxylate sulfate, a betaine surfactant, and an alkyl polyglucoside; and b) at least 8 weight % of the composition of a $C_{12-18}$ fatty alcohol. At this level of fatty alcohol, the composition can have a lotion like appearance in that it is shear thinning, reduced or no amount of stringiness, and the composition can stand up when dispensed.

Also, a cleansing method comprising applying the composition to skin or hair and washing, and optionally rinsing with water.

BRIEF DESCRIPTION OF THE DRAWINGS

FIG. 1 is a rheology profile of 8 weight % fatty alcohol additives in a cleaning composition.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight based on the weight of the composition. The amounts given are based on the active weight of the material.

The composition is particularly well-suited for use as a liquid cleaning composition for personal care, but is also suitable for use as a disinfectant, surgical scrub, hospital hand wash product, hand sanitizer gel, wound care agent, and the like. Use of the composition on inanimate objects (e.g., as a hard surface cleaner) is also possible.

Surfactants

The composition includes surfactants comprising a salt of a $C_{10-16}$ alcohol ethoxylate sulfate, a betaine surfactant, and an alkyl polyglucoside.

In certain embodiments, the combined amount of surfactants are present in an amount of at least 5, 6, 7, 8, 9, 10, 11, 12, or 13 weight % of the composition.

The salt of a $C_{10-16}$ alcohol ethoxylate sulfate can be selected to any one or more of the salt of a $C_{10-16}$ alcohol ethoxylate sulfates. In certain embodiments, the $C_{10-16}$ is lauryl. The average moles of ethylene oxide can be 1-30. Typically, there is an average of 1 to 3 moles of ethylene oxide. The cation for the salt can be any of the typical salt cations, such as sodium, ammonium, alkali metal, alkaline earth metal, triethanolamine, or others. In certain embodiments, sodium is selected.

In certain embodiments, the salt of the $C_{10-16}$ alcohol ethoxylate sulfate comprises sodium lauryl ether sulfate. In certain embodiments, the salt of the $C_{10-16}$ alcohol ethoxylate sulfate comprises sodium lauryl ether sulfate with an average of 2 moles of ethylene oxide. In certain embodiments, the salt of the $C_{10-16}$ alcohol ethoxylate sulfate is present in a quantity that is greater than any other surfactant.

Examples of betaine surfactants include, but are not limited to, one or combinations of cocodimethylcarboxymethylbetaine, cocamidopropylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, and lauryl-bis-(2-hydroxypropyl)-carboxyethylbetaine. In certain embodiments, the betaine surfactant comprises cocamidopropyl betaine.

The alkyl in the alkyl polyglucoside can be any alkyl or combinations thereof, such as decyl, lauryl, or coco. In certain embodiments, the alkyl polyglucoside comprises decyl glucoside.

In certain embodiments, the surfactants comprise, based on a total weight of the surfactants, 60-70 weight % of the salt of a $C_{10-16}$ alcohol ethoxylate sulfate, 20-30 weight % betaine surfactant, and 5-15 weight % alkyl polyglucoside.

In certain embodiments, the surfactants comprise, based on the weight of the surfactants, 66 to 67, or about 66.4, weight % of the salt of a $C_{10-16}$ alcohol ethoxylate sulfate, 24 to 25, or about 24.4, weight % betaine surfactant, and 9 to 10, or about 9.2, weight % alkyl polyglucoside.

Additional surfactants can be included in the composition. Examples of additional surfactants are listed in McCutcheon's Emulsifiers and Detergents, 1993 Annuals, (hereafter McCutcheon's), McCutcheon Division, MC Publishing Co., Glen Rock, N.J.

Fatty Alcohol

The composition comprises at least one $C_{12}$-$C_{18}$ fatty alcohol, preferably a $C_{16}$-$C_{18}$ fatty alcohol. Specific suitable fatty alcohols include but are not limited to lauryl alcohol, myristyl alcohol, cetyl alcohol and stearyl alcohol. The composition can comprise a single type of fatty alcohol or more than one type of fatty alcohol. In certain embodiments, the fatty alcohol comprises stearyl alcohol. It is preferred to use C16 or greater fatty alcohols because in certain are preferred because $C_{12}$-$C_{14}$ fatty alcohol can reduce the amount of foam that is generated.

The composition contains at least 8 weight % fatty alcohol. Certain embodiments of the composition contain the fatty alcohol in an amount of 8-25 wt. %. The composition has the consistency of lotions containing high amounts of emollient oils. Thus, certain embodiments of the inventive composition are free of emollient oils, and yet perform like compositions containing high levels of such oils. At levels below 5 weight %, fatty alcohols can increase viscosity, but at 8 weight % or greater, the composition changes to a lotion like appearance. The lotion like appearance provides a shear thinning composition, a composition with reduced or no stringiness, and the composition can stand up (maintain its shape) when dispensed.

Carrier

The carrier of the composition comprises water, which is preferably demineralized water and/or softened water.

Skin Care Agent

In certain embodiments, the composition can contain 0% to about 5%, and preferably 0.1% to about 3%, by weight, of a skin care agent.

The identity of the skin care agent is not particularly limited, as long as the agent does not adversely affect the stability or efficacy of the composition. One important class of skin care agents is emollients. Emollients are cosmetic ingredients that help to maintain a soft, smooth, and pliable skin appearance. Emollients function by remaining on the skin surface or in the stratum corneum to act as lubricants, to reduce flaking, and to improve skin appearance.

In general, the skin care agent includes polymers (e.g., polyvinylpyrrolidine), protein derivatives (e.g., derivatized hydrolyzed wheat protein), ethoxylated fatty ethers, cellulosics (e.g., hydroxyethylcellulose), and similar skin care agents. For example, suitable skin care agents include, but are not limited to, esters comprising an aliphatic alcohol having 2 to about 18 carbon atoms condensed with an aliphatic or aromatic carboxylic acid including 8 to about 20 carbon atoms, e.g., isopropyl myristate, decyl oleate, and cetearyl isononanate. The ester is either straight chained or branched. Preferably, the ester has a molecular weight of less than about 500 and provides emollient properties.

Non-limiting examples of other skin care agents include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, and palmitamidopropyltrimonium chloride. The above skin care agents can be used alone or in admixture.

Additional Optional Ingredients

The composition also can contain additional optional ingredients well known to persons skilled in the art, such as dyes and fragrances, that are present in a sufficient amount to perform their intended function and do not adversely affect the cleaning efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, preservatives, thickeners, viscosity modifiers, buffering agents, antioxidants, foam enhancers, chelating agents, opacifiers, hydric solvents, hydrotropes, humectants, antimicrobials (see, e.g., U.S. Pat. No. 6,977,082) and similar classes of optional ingredients known to persons skilled in the art.

Specific classes of optional ingredients include alkanolamides as foam boosters; parabens as preservatives; inorganic phosphates, sulfates, and carbonates as buffering agents; EDTA and phosphates as chelating agents; and acids and bases as pH adjusters.

Examples of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

In certain embodiments, the composition is free of inorganic salts, such as sodium chloride. In certain other embodiments, the amount of sodium chloride (and/or all inorganic salts) in the composition is limited to 1 wt. % or less.

An alkanolamide to provide foam enhancement can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

The composition also can contain a preservative in an amount of 0-5 wt. % or 0.01-1 wt. %. Examples of preservatives include, but are not limited to, sorbic acid, potassium sorbate, the parabens (like benzylparaben), imidazolinylurea, methylchloroisothiazolinone, and the hydantoins, like DMDM hydantoin. Additional preservatives as disclosed in the CTFA Handbook at page 78.

The composition can contain an antioxidant and/or an ultra-violet light (UV) absorber, each independently in an amount of 0% to about 0.5% by weight. Examples of antioxidants and UV absorbers include, but are not limited to, BHA, BHT, sodium ascorbate, potassium sulfite, erythorbic acid, benzophenone-1 through benzophenone-12, and PABA. Additional antioxidants and UV absorbers can be found in the CTFA Handbook at pages 78 and 98.

The composition can have a pH that is typical of a skin cleanser, which is usually about 4 to about 9. In certain embodiments, the composition has a pH of 5 to 8, 6 to 8, or 6.5 to 7.5.

The composition can optionally contain humectants. Non-limiting examples of humectants, include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and mixtures thereof.

In certain embodiments, the method comprises applying the composition to the skin or hair, and optionally rinsing with water. In certain other embodiments, the method comprises dispensing the composition from the container in which it is stored.

SPECIFIC EMBODIMENTS

The invention is further described in the following examples. The examples are merely illustrative and do not in any way limit the scope of the invention as described and claimed.

Test Materials

| Tradename | INCI name | Supplier |
|---|---|---|
| Amphosol HCA | Cocamidopropryl betaine (CAP betaine) | Stepan |
| Steol CS-230 | Sodium lauryl ethoxylated sulfate (SLES) | Stepan |
| Lipocol L. | Lauryl Alcohol (C12) | Lipo |
| Lanette 14 | Myristyl Alcohol (C14) | Cognis Corporation |
| Lanette 16 | Cetyl Alcohol (C16) | Cognis Corporation |
| Lanette 18 | Stearyl Alcohol (C18) | Cognis Corporation |

Rheology studies were carried out using a TA instrument AR2000 Rheometer with a 14 mm small vane geometry. A shear rate ramp was used to obtain the viscosity vs. shear stress response.

Light microscopy and imaging were accomplished using an Olympus BX61 motorized compound light microscope mounted with an Olympus DP70 color digital camera accompanied by Olympus/SIS Microsuite Five Software. Shower gel samples were prepared by applying a drop of product onto a glass slide and covering it with a glass coverslip. Samples were examined using the following transmitted light microscopical techniques: brightfield, phase contrast, differential interference contrast and polarized light under crossed polars. Magnification used was 100×.

Comparative Example

A composition representative of conventional liquid cleaning compositions was prepared as a comparative example and as a base for the compositions of the invention. The comparative cleaning composition (hereinafter "CCC") is shown below.

| Ingredient Name | Weight % |
|---|---|
| Water and minors | Q.S. |
| C10-16 Alcohol Ethoxylate, Sulfated, Sodium Salt (SLES) | 8.67 |
| Cocamidopropyl Betaine | 3.17 |
| Alkyl Polyglycoside | 0.83 |
| Sodium Chloride | 0.53 |
| Lauryl Polyglucose | 0.36 |
| 1,3-Bis(Hydroxymethyl)-5,5-Dimethylhydantoin (DMDM Hydantoin) | 0.27 |
| Polyquaternium-7 | 0.21 |
| Tetrasodium EDTA | 0.08 |
| Total Materials | 100 |

Example 1

High levels of fatty alcohol turned CCC from a non-structured viscous liquid into a structured, shear-thinning gel. The resulting product has a lotion-like appearance.

The shear viscosity of shower gel samples were investigated using a range of shear rates (D), from 0.01 to 30 sec$^{-1}$. Gels and non-structured viscous fluids can easily be distinguished by measuring their flow behavior. Structured fluids exhibit non-Newtonian behavior, while non-structured fluids do not.

FIG. 1 shows the rheological profiles of 8% fatty alcohols in CCC in the absence of any salt. The control is CCC with 1% NaCl. CCC (with no salt) cannot be directly used as a control because of its low viscosity (about 32.5 cps). All of the fatty alcohols turned CCC from a viscous liquid into a structured gel, with the impact of C12 alcohol being the most dramatic.

Example 2

A 15% fatty alcohol containing CCC was prepared, and a polarized microscopy image was taken (not shown). When polarized light passes through anisotropic crystals, it decomposes into two rays resulting in birefringence. This fatty alcohol containing formula contains well dispersed, fine anisotropic crystals, resulting in a smooth, rich lotion-like appearance.

What is claimed is:

1. An aqueous composition comprising
   a) surfactants comprising a salt of a $C_{10-16}$ alcohol ethoxylate sulfate, a betaine surfactant, and an alkyl polyglucoside; and
   b) at least 8 weight % of the composition of a $C_{12-18}$ fatty alcohol.

2. The composition of claim 1, wherein the surfactants are present in an amount of at least 5 weight % of the composition.

3. The composition of claim 1, wherein the salt of the $C_{10-16}$ alcohol ethoxylate sulfate is present in a quantity that is greater than any other surfactant.

4. The composition of claim 1, wherein the salt of the $C_{10-16}$ alcohol ethoxylate sulfate comprises sodium lauryl ether sulfate.

5. The composition of claim 1, wherein the salt of the $C_{10-16}$ alcohol ethoxylate sulfate comprises sodium lauryl ether sulfate with an average of 2 moles of ethylene oxide.

6. The composition of claim 1, wherein the betaine surfactant comprises cocamidopropyl betaine.

7. The composition of claim 1, wherein the alkyl polyglucoside comprises decyl glucoside.

8. The composition of claim 1, wherein the surfactants comprise, based on a total weight of the surfactants, 60-70 weight % of the salt of the $C_{10-16}$ alcohol ethoxylate sulfate, 20-30 weight % betaine surfactant, and 5-15 weight % alkyl polyglucoside.

9. The composition of claim 1, wherein the surfactants comprise, based on the weight of the surfactants, 66 to 67 weight % of the salt of the $C_{10-16}$ alcohol ethoxylate sulfate, 24 to 25 weight % betaine surfactant, and 9 to 10 weight % alkyl polyglucoside.

10. The composition of claim 1, wherein the fatty alcohol comprises stearyl alcohol.

11. The composition of claim 1, wherein the composition contains 1 weight % or less of sodium chloride.

12. The composition of claim 1, wherein the composition contains 1 weight % or less of an inorganic salt.

13. A cleansing method comprising applying the composition of claim 1 to skin or hair and washing.

14. The composition of claim 1, wherein the surfactants consist of the salt of a $C_{10-16}$ alcohol ethoxylate sulfate, the betaine surfactant, and the alkyl polyglucoside.

* * * * *